US010538577B2

(12) United States Patent
De Silanes Perez et al.

(10) Patent No.: US 10,538,577 B2
(45) Date of Patent: Jan. 21, 2020

(54) POLYVALENT IMMUNOTHERAPEUTICS

(71) Applicant: INOSAN BIOPHARMA S.A., Mexico City (MX)

(72) Inventors: Juan Lopez De Silanes Perez, Mexico (MX); Jesús Raúl Soria Osorio, Mexico City (MX)

(73) Assignee: INOSAN BIOPHARMA S.A., Juarez (MX)

( * ) Notice: Subject to any disclaimer, the term of this patent is extended or adjusted under 35 U.S.C. 154(b) by 0 days.

(21) Appl. No.: 13/761,480

(22) Filed: Feb. 7, 2013

(65) Prior Publication Data

US 2016/0368969 A1 Dec. 22, 2016

(30) Foreign Application Priority Data

Oct. 18, 2012 (MX) .................... MX/a/2012/012132

(51) Int. Cl.
*A61K 39/395* (2006.01)
*C07K 16/06* (2006.01)
*C07K 16/18* (2006.01)

(52) U.S. Cl.
CPC ............ *C07K 16/065* (2013.01); *C07K 16/18* (2013.01); *C07K 2317/35* (2013.01); *C07K 2317/54* (2013.01)

(58) Field of Classification Search
None
See application file for complete search history.

(56) References Cited

U.S. PATENT DOCUMENTS

| 2,065,196 | A | 12/1936 | Parfentjev |
| 2,123,198 | A | 7/1938 | Parfentjev |
| 2,175,090 | A | 10/1939 | Parfentjev |
| 4,849,352 | A | 7/1989 | Sullivan et al. |
| 5,733,742 | A | 3/1998 | Landon |
| 6,709,655 | B2 | 3/2004 | Lopez De Silanes et al. |
| 7,485,303 | B2 | 2/2009 | De Silanes et al. |
| 8,048,414 | B1 | 11/2011 | Sullivan et al. |
| 8,075,893 | B2 | 12/2011 | Lopez De Silanes et al. |
| 8,287,860 | B2 | 10/2012 | Rodriguez et al. |
| 8,512,706 | B2 | 8/2013 | Lopez De Silanes et al. |
| 8,541,551 | B2 | 9/2013 | Rodriguez et al. |
| 2002/0164327 | A1 | 11/2002 | Silanes et al. |
| 2004/0166107 | A1 | 8/2004 | De Silanes et al. |
| 2006/0210563 | A1 | 9/2006 | Lopez De Silanes et al. |
| 2009/0142356 | A1 | 6/2009 | Lopez De Silanes et al. |
| 2011/0177078 | A1 | 7/2011 | Rodriguez et al. |
| 2012/0064063 | A1 | 3/2012 | Lopez De Silanes et al. |
| 2013/0071399 | A1 | 3/2013 | Rodriguez et al. |

FOREIGN PATENT DOCUMENTS

| CN | 101816789 | 9/2010 |
| IN | 188098 B | 8/2002 |
| WO | WO 2004/07695 | 9/2004 |
| WO | 2007/114680 | 10/2007 |

OTHER PUBLICATIONS

UK HealthCare, Crotalidae Polyvalent Antivenin Protocol, p. 1-3, 2008.*
Anonymous "CroFab® crotalidae polyvalent immune Fab (ovine)" prescribing information, eight pages (Mar. 2012).
Anonymous "ANAVIP crotalidae immune F(ab')₂ (equine)" prescribing information, eight pages (May 2015).
Boyer "Subacute coagulopathy in a randomized, comparative trial of Fab and F(ab')₂ antivenoms" Toxicon 74:101-108 (Aug. 2013).
Bush et al. "Comparison of F(ab')₂ versus Fab antivenom for pit viper envenomation: A prospective, blinded, multicenter, randomized clinical trial" Clin. Toxicol. 53:37-45 (Oct. 2014).
Gutierrez, J.M. et al., "Antivenoms for the treatment of snakebite envenomings: The road ahead." Biologicals, 39(3): 129-142 (2011).
Jones, R.G, Landon, J. "A protocol for 'enhanced pepsin digestion': a step by step method for obtaining pure antibody fragments in high yield from serum." Journal of Immunological Methods, 275(1-2):239-250 (2003).

* cited by examiner

*Primary Examiner* — Yunsoo Kim
(74) *Attorney, Agent, or Firm* — Nixon & Vanderhye P.C.

(57) ABSTRACT

The invention is related to the production and development of a lyophilized injectable formulation of modified antibodies or their variants, highly specific neutralizers of heterologous mixtures of proteins, peptides and other organic or inorganic components have different specific activities and may include but are not limited to the venoms of venomous animals. For convenience, we refer to venoms, but all type of venoms was included of land and marine animals. It is also addressed to the production method which includes the hyperimmunization of mammals for the production of highly specific antibodies, the modification (fragmentation) and purification process, and finally the injectable formulation conferring thereon properties of high purity and high specificity.

19 Claims, 13 Drawing Sheets

ANTIVENOM OF THE
INVENTION

| Batch | Total Protein Amount (mg) | B. asper specific anti-venom antibodies percentage | C. durissus specific anti-venom antibodies percentage |
|---|---|---|---|
| A | 133 | 17.8 | 19.4 |
| B | 126 | 15.6 | 21.6 |
| C | 118 | 19.2 | 17.3 |
| D | 135 | 18.5 | 19.7 |
| E | 138 | 17.3 | 20.7 |
| Average | 130.0 | 17.7 | 19.7 |
| St. Dev. | 7.2 | 1.2 | 1.4 |

PRIOR ART
ANTIVENOMS

| Batch | Total Protein Amount (mg) | Percentage of antibodies specific to venom of Species 1 | Percentage of antibodies specific to venom of Species 2 |
|---|---|---|---|
| Producer I Batch A | 943 | 4.3 | 3.7 |
| Producer I Batch B | 979 | 4.4 | 4.8 |
| Producer II Batch A | 922 | N.A. | N.A. |
| Producer III Batch A | 374 | 12.4 | 10.1 |
| Producer IV Batch A | 275 | 13.8 | 8.7 |

Species 1 and 2 correspond to venoms used in the immunization mixture

Fig. 1

ANTIVENOM OF THE
INVENTION

| Batch | Total Protein Amount (mg) | AV mg necessary to neutrilize one mg of venom of B. asper | AV mg necessary to neutrilize one mg of venom of C. durissus |
|---|---|---|---|
| A | 133 | 6.6 | 11.9 |
| B | 126 | 6.3 | 11.3 |
| C | 118 | 5.9 | 10.5 |
| D | 135 | 6.7 | 12.1 |
| E | 138 | 6.8 | 12.3 |
| Average | 130.0 | 6.4 | 11.6 |
| St. Dev. | 7.2 | 0.4 | 0.6 |

PRIOR ART
ANTIVENOMS

| Batch | Total Protein Amount (mg) | AV mg necessary to neutrilize one mg of venom of Specie 1 | AV mg necessary to neutrilize one mg of venom of Specie 2 |
|---|---|---|---|
| Producer I Batch A | 943 | 47.2 | 31.4 |
| Producer I Batch B | 979 | 49.0 | 32.6 |
| Producer II Batch A | 922 | 22.0 | 34.9 |
| Producer III Batch A | 374 | 9.0 | 18.2 |
| Producer IV Batch A | 275 | 13.6 | 24.6 |

Species 1 and 2 correspond to venoms used in the immunization mixture

Fig. 2

POLYVALENT IMMUNOTHERAPEUTICS

This application claims priority benefit of Mexican Application No. MX/a/2012/012132, filed 18 Oct. 2012; the entire contents of which are hereby incorporated by reference.

FIELD OF THE INVENTION

The present invention is related to polyvalent immunotherapeutics of high specificity, the modification of antibodies and the production process involved.

BACKGROUND OF THE INVENTION

Poisonings by venomous animals are recognized as a problem of public health in some regions of the planet where the interaction of man with these animals is frequent. We can consider animals producing pharmacological substances which can interfere with our survival as venomous and/or venomous animals. The venoms most studied are those coming from snakes, scorpions, spiders, mollusks and microorganisms, however other venomous animals exist including fish, frogs, insects, anemones and corals, among others.

The antidotes based on manipulation of the immune system of mammals have been used to counteract the effects of the venom, where immunoglobulins or antibodies play the central role. In 1888 Emilie Roux and Alesandre Yersin demonstrated that the blood of animals immunized against diphtherial toxins provided protection to animals when defied against toxins. By 1890 Emil von Behring and Shibasaburo Kitasato confirmed the transfer of passive immunity against diphtheria and tetanus toxins; this year is considered the commencement of serum-therapy and is also thought of as the first generation of anti-venom, the second generation corresponds to purified immunoglobulins from serum and the following generation consists of immunoglobulin fragments.

The production of F(ab')2 fragments and Fab, has been described in literature since the beginning of the last century, in 1936 I. A. Parfentjev (U.S. Pat. Nos. 2,065,196, 2,123,198 and 2,175,090). The majority of the methods are based on utilizing the physiochemical and thermodynamic properties of proteins, such as solubility, form and affinity. Therefore over the course of recent years some action has existed for the production of antibody fragments F(ab')2 and Fab, as in the case of Landon U.S. Pat. No. 5,733,742, Sullivan et al., and U.S. Pat. No. 4,849,352.

However, the current development of protein analysis technologies has become a tool for the development and improvement of antibodies modified by enzymatic digestion, because they have allowed further characterization of the immunogens employed in the production of hyperimmune mammal plasmas, as well the quantification process of the neutralizing activity of specific antibodies, and control of the purification process.

The production of modified antibodies (fragments) takes placed when the immunoglobulins (IgG) are enzymatically digested guided by different proteolytic enzymes such as pepsin or papain, eliminating the fraction Fc in both cases but, in the case of pepsin, a fragment F(ab')2 is obtained and in the case of papain, two fragments Fab. These fragments F(ab')2 retain the characteristics of the complete antibodies with respect to their specificity, affinity and stability. In addition to the absence of region Fc from the antibodies, the appearance of adverse effects (such as, for example, anaphylactic reactions), is eliminated due to the fact that the Fc region bonding to various cell receptors such as the Fc receptor and other molecules of the immunity system such as the proteins of the complement, as well as other effector functions such as opzonization, cell lysis and the degranulation of the mast cell, basophils and eosinophils.

The Mexican patent MX230257 by J. Lopez de Silanes et al. of the Instituto Bioclon (Bioclon Institute), and its equivalents U.S. Pat. Nos. 6,709,655, 7,485,303 and 8,075,893, refer to the method for preparing a pharmaceutical composition comprising F(ab')2s fragments, presenting unique characteristics acquired by the preparation method which is free of:

Complete antibody molecules
Proteic molecules of another nature
Albumin
Fibroinogen
Viral particles and
Pyrogens However, not just any fabotherapeutic product comes within the scope of patent MX230257 and its United States equivalents.

OBJECTIVE OF THE INVENTION

One objective of the invention is related to the production and development of a highly modified specific antibody formulation obtained from mammals.

Another objective of the present invention refers to the production and development of a lyophilized formulation of modified antibodies, highly specific or variable thereof obtained from mammals.

Another objective of the invention is related to the production and development of highly specific neutralizing modified formulation of modified antibodies, highly specific neutralizing from heterologous proteins mixtures, peptides and other organic and inorganic components having different specific activities and they may include, but are not limited to, venoms of venomous animals.

Another objective of the present invention includes a useful production method for the hyperimmunization of horses for the production of highly specific antibodies, a modification process (fragmentation) and purification.

Another objective of the invention is to endow the lyophilized injectable formulation, with high purity and high specificity properties.

Other objectives and aspects of the present invention will be obvious to people of ordinary skills on considering this disclosure.

BRIEF DESCRIPTION OF THE DRAWINGS

FIG. 1. It shows two comparison charts of anti-venom of the present invention for *B. apser* and *C. durissus* species of snake against anti-venom of the state of the art. The percentage of specific antibodies against venom utilized in immunization of antibodies-producing horses is shown for the purpose of making clear what percentage of the immunoglobulin's present in a vial of the batches used is bonded to the venoms.

FIG. 2. It shows two comparison charts of anti-venom of the present invention for *B. apser* and *C. durissus* species of snake against anti-venom of the state of the art. It gives the amount in milligrams of the anti-venoms necessary to neutralize a milligram of venom used in the immunization of antibodies-producing horses.

DETAILED DESCRIPTION OF THE INVENTION

Figure 3:
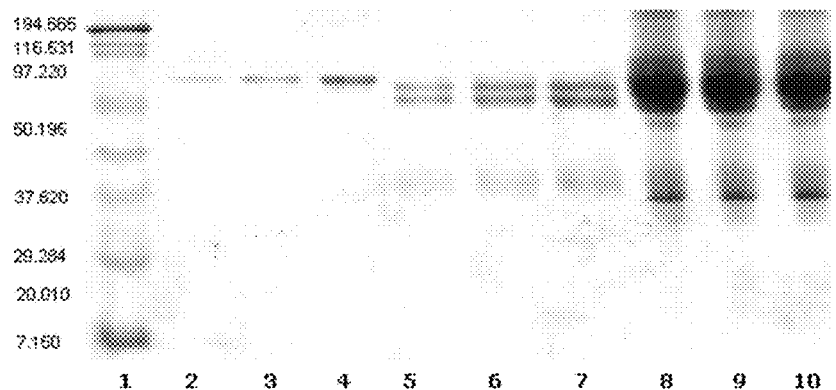
FIG. 3. The electrophoresis in the conditioning stage of the hyperimmune plasma before enzymatic hydrolysis. Lane 1, is the molecular weight marker. Lane 2, 0.5% albumin standard. Lane 3, 1.0% albumin standard. Lane 4 3.0% albumin standard, 4.IgG+IgGT at 3%. Lane 5, IgG+IgGT at 5%. Lane 6, IgG+IgGT at 7%. Lane 7, IgG+IgGT at 10%. Lane 8, Batch 1 of conditioned plasma before enzymatic hydrolysis. Lane 9, Batch 1 of the conditioned plasma before enzymatic hydrolysis. Lane 10, Batch 1 of the conditioned plasma before enzymatic hydrolysis.

For better comprehension and understanding, definitions are provided of the terms used in the present invention; however these definitions do not limit the scope of the invention.

"Lyophilized Injectable Formulation". It refers to a lyophilized injectable pharmaceutical form which is sterile, free from contamination (physical, chemical, microbiological and biological) with elevated purity of over 85%, with a total concentration of proteins not above 5%, free of components of mammalian plasma and complying with the specifications for concentration, quality, purity, innocuousness and potency established in the Pharmacopoeia of the United Mexican States (FEUM) and in the United States Pharmacopeia (USP), for intramuscular or intravenous application.

"Modified Antibodies". It refers to the G-type immunoglobulins which are modified by eliminating the fraction crystallizable (Fc) and generating a bivalent fragment of the F(ab')2 type which eliminates the risk of adverse reactions and are highly specific against the complex antigenics generated by the initial immunoglobulins.

"High specificity". To achieve an immunotherapeutic of high specificity it is necessary that hyperimmune plasmas, which are the matter of those produced, possess very high neutralizing titles. The high neutralizing titles of the plasma force the anti-venom to neutralize the same quantity of venom with lesser quantities of anti-venom, resulting in greater security for the patients due to receiving lower quantities of heterologous proteins. The high neutralizing titles of the plasma are obtained through five principal factors: (1) The utilization of highest quality certified venoms. (2) The use of immunizing venoms obtained from a higher number of individuals of the same venomous species and geographically different areas, in order for a good coverage of the biochemical diversity of the composition of the venoms. (3) The rational and alternate use of adjuvants with different mechanisms of action. 4) The maturing of the humoral immune response over the course of several months (at least six). (5) an optimum maintenance and handling of the horses producing the hyperimmune plasma, including a balanced diet, exercise, friendly handling and, very important, the realization of plasmapheresis (return of the globular package) within a period not to exceed 120 minutes.

"Complex antigens". They are the heterologous mixtures of proteins, peptides and other organic and inorganic compounds having different specific activities and may include but are not limited to arachnids, snakes, birds, fish, crustaceans, insects, frogs, anemones and corals, among others.

"Hyperimmunization". It refers to the systematic process of innoculation (dosage, frequency, method of administration) of an immunogenic mixture (which can be formed by proteins, peptides and other organic and inorganic compounds) for the production of specific immunoglobulins. Also includes the methodology and experimental strategy for the control and analysis of the specific neutralizing activity of the immunoglobulins.

Methodology

According to the foregoing description, the first stage consists of the production of immunoglobulins from the hyperimmunization with previously treated and processed complex antigens of mammals such as horses, sheep, goats and rabbits, among others, with specific methodologies of detoxification such as, for example, radiation with gamma rays. In addition to follow-up in immunization schemes designed to achieve the maximum specificity. Followed by a modified antibodies production process in which the Fc fraction is eliminated by an enzymatic digestion, utilizing a proteolytic enzyme which, in this case, is the pepsin.

The production process consists of 9 stages, the first stage of which is dilution of the plasma in three volumes of saline isotonic solution (0.85%) pre-treated with thimerosal, followed by an adjustment of the pH conditions from 3.5 to 4.0 and at a temperature of from 18 to 20° C. Subsequently add an acid solution of pre-treated and pre-activated pepsin to achieve a final pepsin concentration of 0.9 to 1.1% (with at least 400 UI/g) and maintain the conditions during 180 minutes to complete elimination of the Fc fraction from the immunoglobulins (production of F(ab')2 Fragments). This is verified by a SDS-PAGE analysis with a maximum concentration of IgG of 2% and a maximum concentration of albumin (the most highly concentrated protein in the plasma of mammals) no greater than 0.5%. At this stage the enzymatic digestion process hydrolizes the proteins of greater molecular size such as albumin, fibrinogen and other coagulation factors present in the hyperimmune plasma, converting these into small peptides with an approximate molecular weight of 15 KDa.

An aqueous solution of ammonium sulfate 50% is subsequently added (previously filtered through a cellulose 0.2 micron filter), to eliminate the possibility of microbial contamination, in order to achieve a final saturation concentration of 35% at a temperature of 2 to 8° C., for the purpose of favoring precipitation of the low molecular weight (under 15 KDa) components. Once the solution is precipitated by a depth filtration module of modified cellulose fiber containing a final nominal filtration gradient of 100 to 0.8 microns and complying with US Code of Federal Regulations Title 21, parts 177.2260 e, f, g, h, i, j, k, l, and the plastic components are included in the US Code of Federal Regulations Title 21, part 177.1520.

The filtrate obtained is stored at 2° C. to 8° C. and the pH has been adjusted between 6.8 to 7.0 and subsequently diafiltered it by means of tangential flow filtration equipment utilizing a polyethersulfone membrane of 50 Kda and using a borates buffer as diafiltration buffer. This process is carried out in continuous operation maintaining a diafiltration sheer under 1000 sec−1, allowing the elimination of the ammonium sulfate utilized in the precipitation also eliminating the components of low molecular weight (under 15 KDa) which could be present after the enzymatic digestion. The diafiltered product is recovered in sterile and pyrogen-free containers, and is filtered through a filter of 20 nanometers pore size; this operation is called nanofiltration due to the size of the pores on the nanometer order. The purpose of the nanofiltration is to eliminate the possible viral charge present. Once the product has been nanofiltered, the cryopreservation and isotonicity regulating agents are added in a unitary operation called Formulation, in which mannitol 9 mg/mL, Alanine 18 mg/mL and Polysorbate 80 0.1 mg/mL are added. Finally the product is filtered in an area classified as aseptic through a PVDF filter of 0.1 micron to eliminate any possible microbial contamination, in an operation called terminal aseptic filtration. The formulated product is dosed in type 1 vials complying with FEUM and USP requirements. The dosing products under aseptic conditions is lyophilized under standard conditions (freezing up to −40° C. for 8 hours and a primary drying at −5° C. with a speed gradient of +5.2° C./hour, and a secondary drying at 45° C. for 10 hours at a speed of 9° C./hour). These conditions allow the elimination of up to 98% of the water content, as an advantage in addition to the elimination of water the product stability is increased, further it allows them to maintain the biological properties. The lyophilized product is evaluated in different tests including tightness, residual humidity and a 100% visual inspection to determine the presence of particles, in addition to an analysis of all the quality specifications established for a lyophilized injectable product which include: sterility, innocuousness, security and neutralizing potency.

The following examples are given as a means to illustrate the present invention, without limiting the scope of same.

Example 1

Hyperimmunization of horses and the production of high specificity immunoglobulins employing the method of the present invention.

FIG. 1 shows two comparison charts of anti-venom of the present invention for the *B. apser* and *C. durissus* species of snake against anti-venom of the state of the art in percentage terms. The experimental measurement was taken by affinity chromatography in the following manner: each one of the venoms covalently was coupled to Sepharose 4B particles activated by cyanogen bromide. Columns of affinity with the corresponding Sepharose 4B-Venom particles were mounted. 10 mg of each one of the anti-venom batches indicated was passed. The unspecific immunoglobulins pass through the affinity column without interacting with the venom. The specific immunoglobulins (specific antibodies) are bonded with the venom in the column and are eluted with 100 mM of acetic acid. Both the quantity of unspecific immunoglobulins and that of the specific antibodies are measured to calculate the percentage of specific antibodies. A higher percentage of specific antibodies mean better quality anti-venom, since it predicts the use of a lesser quantity of protein to achieve the therapeutic effect and, therefore, a greater security of the anti-venom.

The anti-venom product of the present invention (high specificity immunotherapeutics) have, on average 17.7 and 19.7% of specific antibodies, respectively, for each one of the venoms utilized in the immunization of the horses.

The anti-venom of the state of the art fluctuated between 4.3 and 13.8% of specific antibodies for one species of snake and between 3.7 and 10.1% for the other. The total amount of protein per vial is lower when the percentage of specific antibodies is higher, and vice versa.

Example 2

Determination of the high specificity of immunoglobulins produced in hyperimmunized horses, utilizing the method of the present invention.

FIG. 2 shows comparison charts of anti-venom of the present invention for the *B. apser* and *C. durissus* species of snake, against anti-venom of the state of the art. The amount is shown in milligrams of the anti-venom necessary to neutralize a milligram of venom utilized in the immunization of antibodies-producing horses. The experiment was determined by utilizing the effective average doses (DE50s) against three average lethal doses (DL50s), following the conditions and protocols described in Casasola et al, 2009. The DE50s are obtained as microliters of venom in order to neutralize three LD50s and, as the concentration of proteins of the anti-venom is known, the DE50s can be calculated as amounts of protein. The LD50s have their equivalent in venom mass, therefore the conversion to the mg of anti-venom necessary to neutralize a milligram of venom is direct.

In this case, the fewer milligrams of anti-venom necessary to neutralize one mg of venom, the anti-venom is greater since a lesser quantity of anti-venom is needed to achieve the same effectiveness.

The high specificity immunotherapeutics of the present invention need on average, 6.4 and 11.6 mg, respectively, to neutralize the two venoms utilized to immunize the horses. While the anti-venom of the state of the art require between 9 and 49 mg to neutralize one of the species and between 18.2 and 34.9 for the other.

Example 3

Evaluation and control of the production of modified antibodies (F(ab')2 fragments) by applying the process of the present invention.

Figure 4:
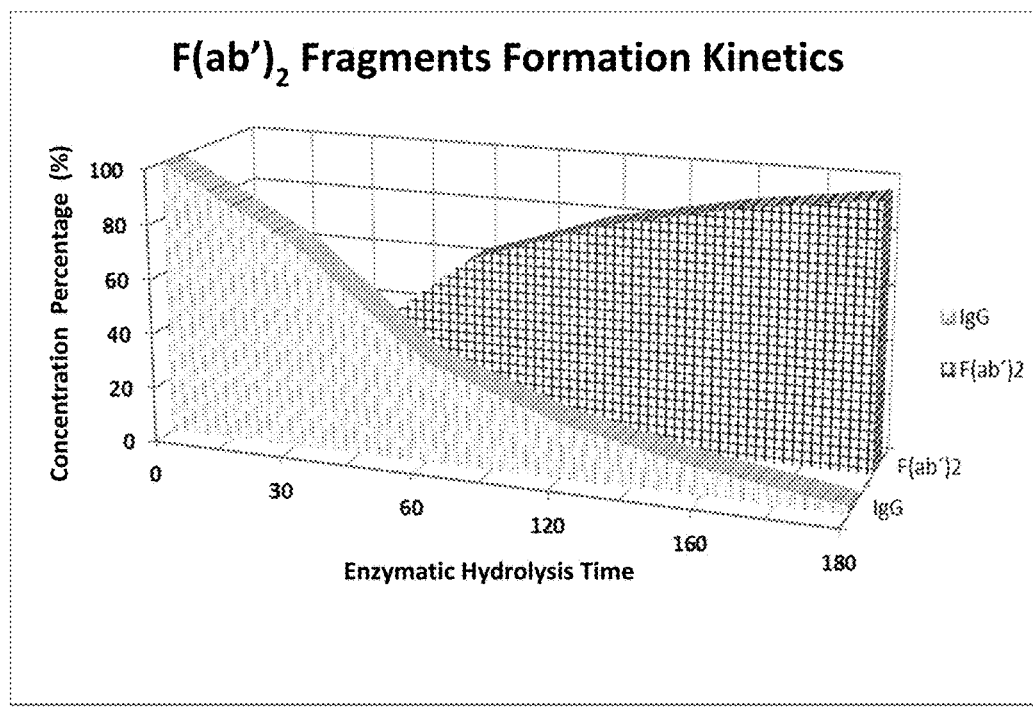
FIG. 4. The graph showing the formation of F(ab')2 fragments during enzymatic digestion with pepsin.
Figure 5:
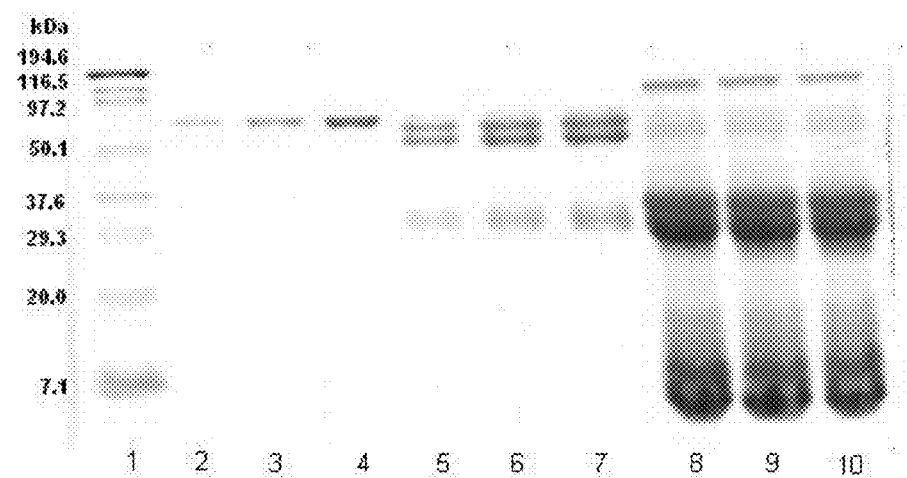
FIG. 5. The electrophoresis (SDS-PAGE) for three test batches after enzymatic digestion with pepsin. Lane 1, Molecular weight marker. Lane 2, 0.5% Albumin standard. Lane 3, 1.0% Albumin standard. Lane 4, 3.0% Albumin standard, 4.IgG+IgGT at 3%. Lane 5, IgG+IgGT at 5%. Lane 6, IgG+IgGT at 7%. Lane 7, IgG+IgGT at 10%. Lane 8, Batch 1 of plasma digested with pepsin for the production of F(ab')2 fragments. Lane 9, Batch 2 of plasma digested with pepsin for the production of F(ab')2 fragments Lane 10, Batch 3 of plasma digested with pepsin for the production of F(ab')2 fragments.
Figure 6A:
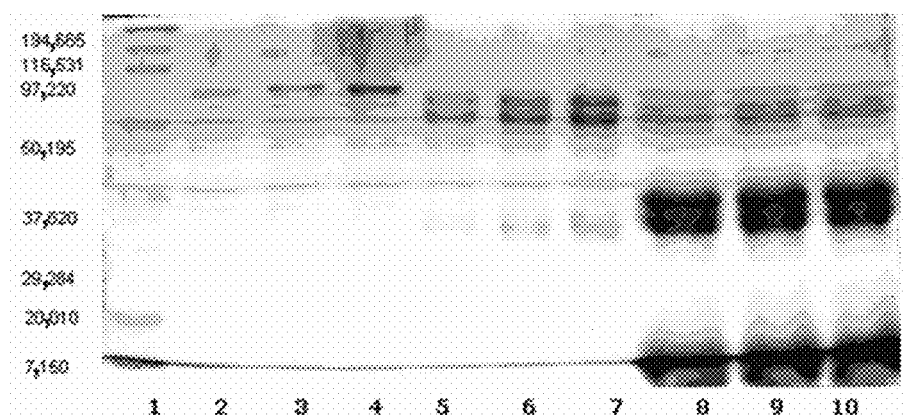
FIGS. 6A to 6B. The precipitation stage with Ammonium Sulfate SDS-PAGE Electrophoresis for three batches of development after the precipitation with ammonium sulfate in FIG. 6A. It is shown by the Salting-out technique the extraction of non-F(ab')2 proteins (such as pepsin, undigested fibrinogens, complete IgG and the production of a large number of peptides during digestion), in an ammonium sulfate solution of 35% (w/v). Lane 1, Molecular weight marker. Lane 2, 0.5% Albumin standard. Lane 3, 1.0% Albumin standard. Lane 4, 3.0% Albumin standard, 4.IgG+IgGT at 3%. Lane 5, IgG+IgGT at 5%. Lane 6, IgG+IgGT at 7%. Lane 7, IgG+IgGT at 10%. Lane 8, First batch of supernatant following the precipitation with ammonium sulfate. Lane 9, Second batch of supernatant following the precipitation with ammonium sulfate. Lane 10, Third batch of supernatant following the precipitation with ammonium sulfate. Also shown in FIG. 6B is a chromatogram obtained from an analysis of molecular exclusion HPLC showing the composition of the supernatant at this stage, consisting of F(ab')2 fragments and low molecular weight components (under 20 KDa).
Figure 6B:
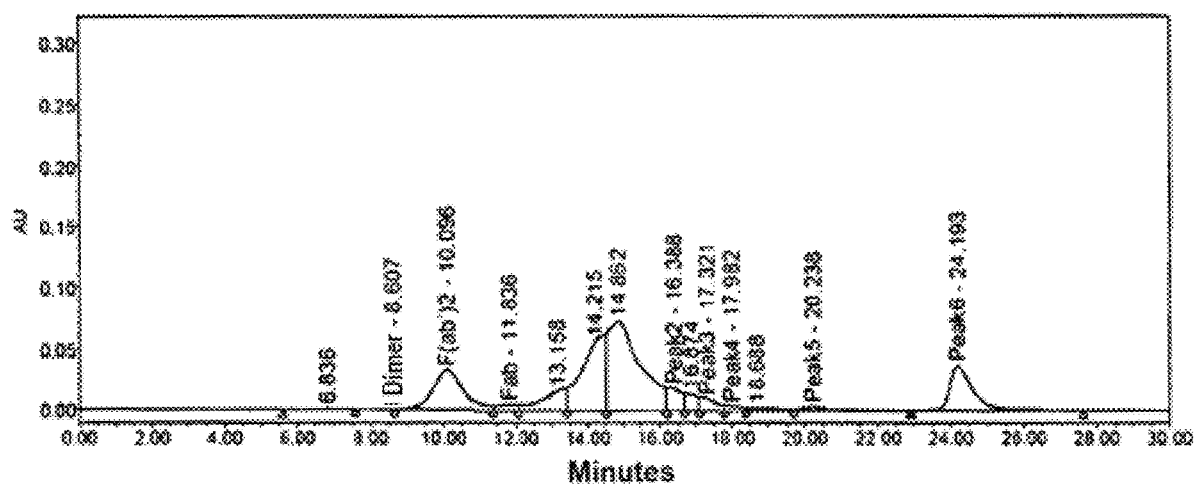
Figure 7:
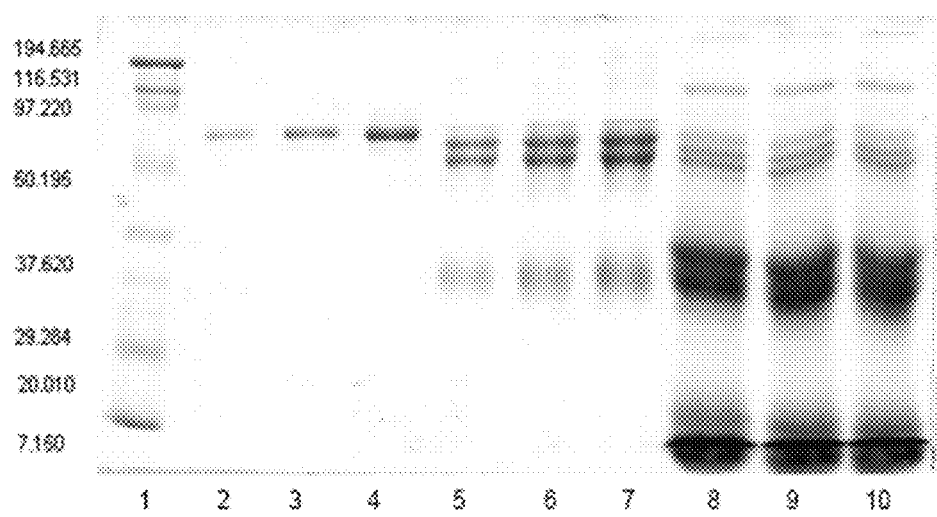
FIG. 7. Depth filtration stage. Electrophoretic analysis (SDS-PAGE) and chromatographic analysis (GE-HPLC) of the clarified soluble stage, respectively. The results show a reduction in the components of high molecular weight (HMWC) below 0.45%. SDS-PAGE Electrophoresis of three batches of development in the depth filtration stage. Lane 1, Molecular weight markers. Lane 2, 0.5% Albumin standard. Lane 3, 1.0% Albumin. Lane 4, 3.0% Albumin. Lane 5, IgG+IgGT at 3%. Lane 6, IgG+IgGT at 5.0%. Lane 7, IgG+IgGT at 7%. Lane 8, Clarified Batch 1. Lane 9, Clarified Batch 2. Lane 10, Clarified Batch 3.
Figure 8A:
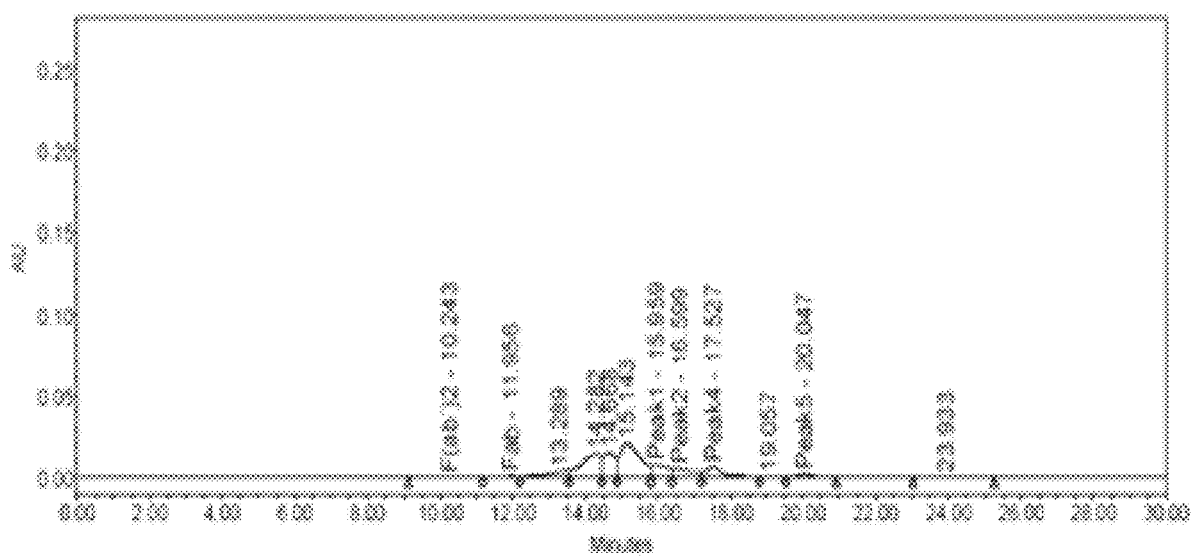
FIGS. 8A to 8F. Diafiltration stage. This stage eliminates the ammonium sulfate and the greater part of low molecular weight peptides present in the product and effects a balance in the isotonicity of the F(ab')2 fragments with 0.85% isotonic saline solution. At the end of this stage, the product is concentrated for removing solvent by forced diafiltration. The results of percentage composition are presented during the diafiltration process. The HPLC analysis for permeate of the Ultrafiltration Stage of the product in the process. Permeate for 0 diafiltrations in FIG. 8A, Permeate for 2 diafiltrations in FIG. 8B, Permeate for 4 diafiltrations in FIG. 8C, Permeate for 6 diafiltrations in FIG. 8D, Permeate for 8 diafiltrations in FIG. 8E, and Permeate for 10 diafiltrations in FIG. 8F.
Figure 8B:
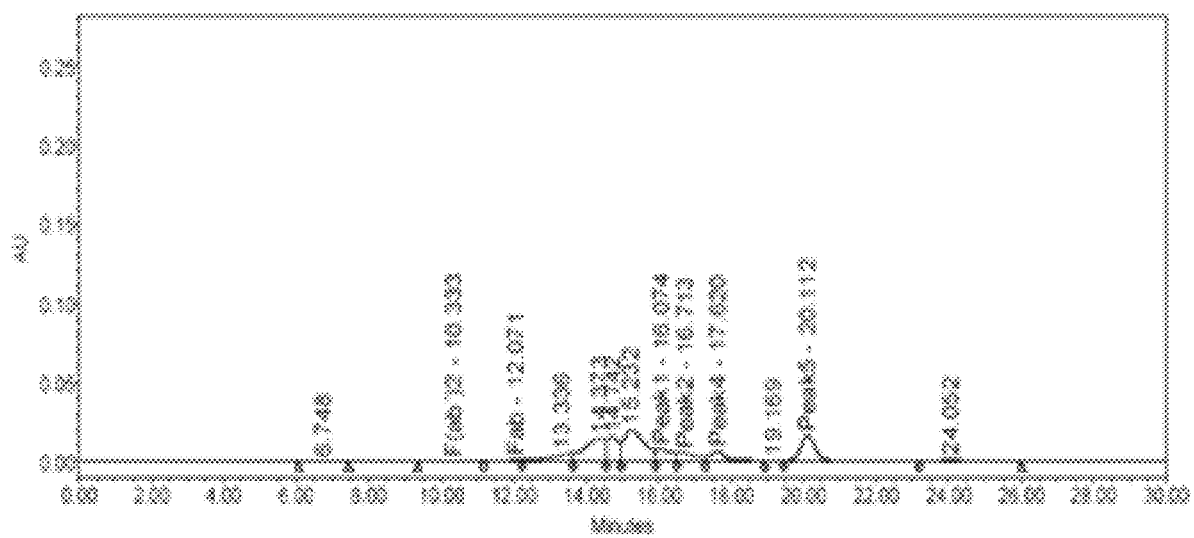
Figure 8C:
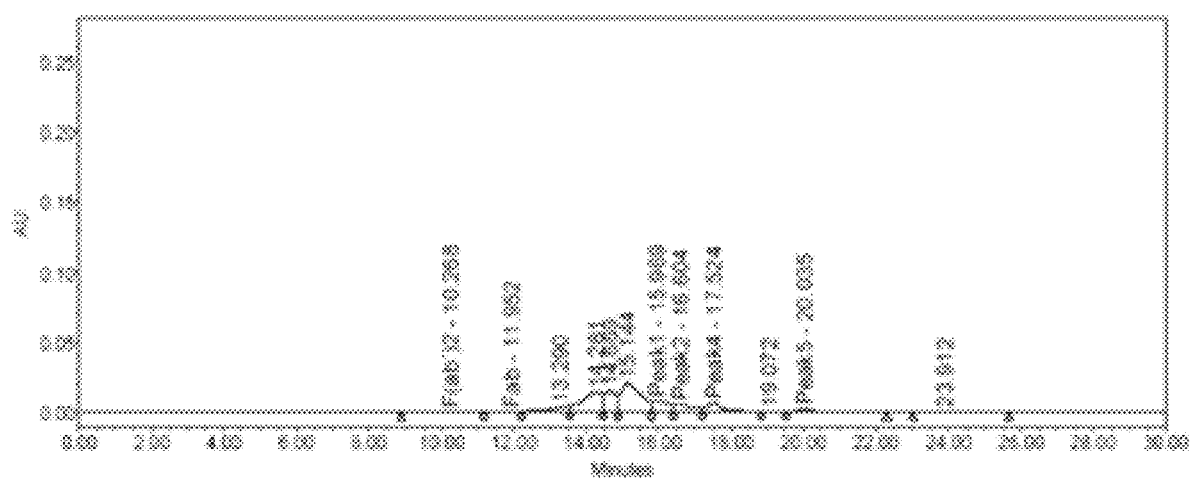
Figure 8D:
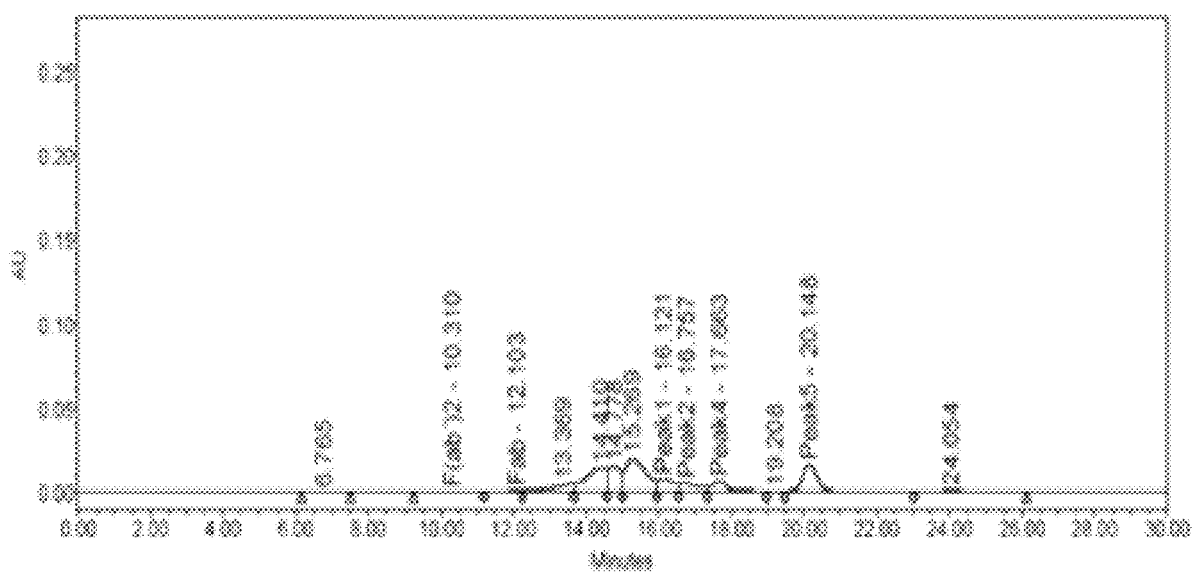
Figure 8E:
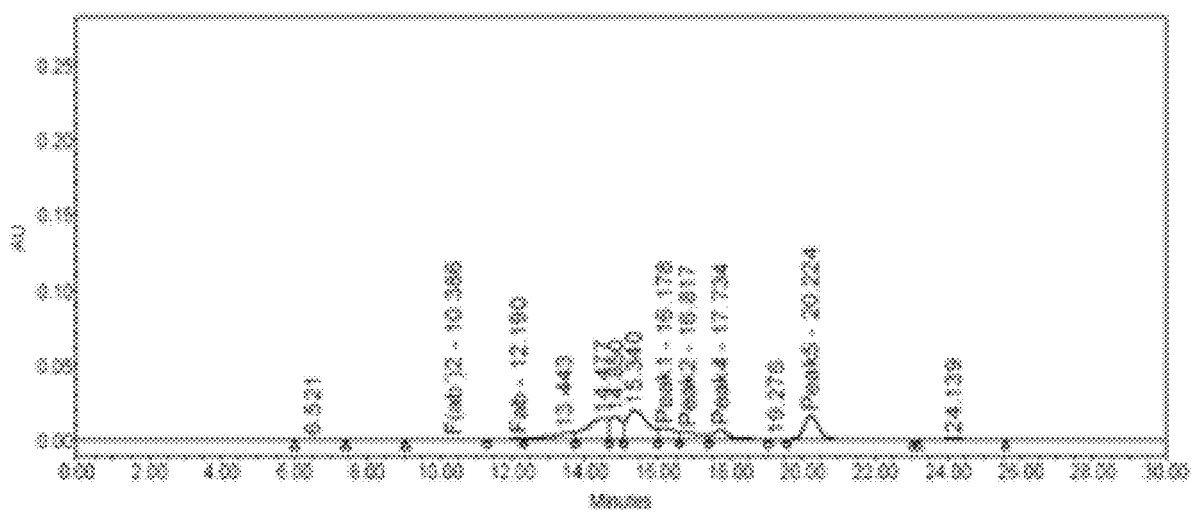
Figure 8F:
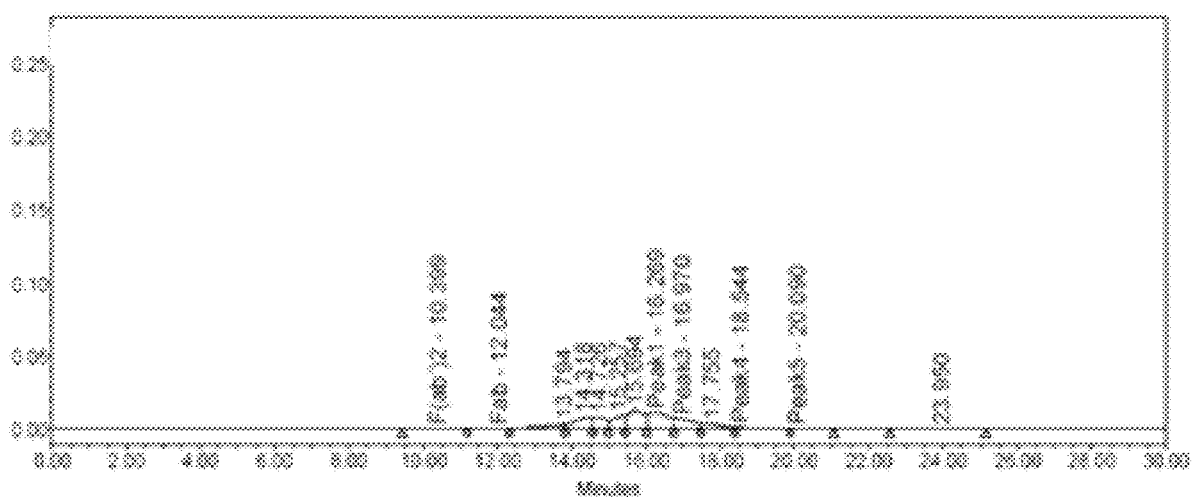
Figure 9:
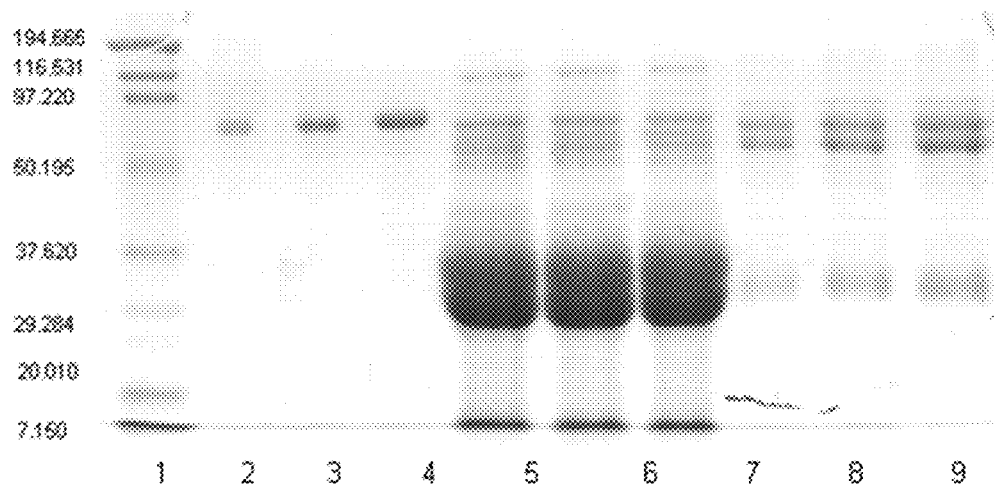
FIG. 9. SDS-PAGE Electrophoresis for the three batches at the diafiltration stage and HPLC analysis for the ultrafiltered product in the process. Lane 1, Molecular weight marker. Lane 2, 0.5% Albumin. Lane 3, 1.0% Albumin. Lane 4, 3.0% Albumin, 4.IgG+IgGT 3%. Lane 5, Ultra-filtered product in the process of batch 1. Lane 6, Ultra-filtered product in the process of batch 2. Lane 7, Ultra-filtered product in the process of batch. Lane 8, IgG+IgGT at 3.0%. Lane 9, IgG+IgGT at 5.0%. Lane 10, IgG+IgGT at 7.0%.

FIG. 3 shows the SDS-PAGE analysis under reducing conditions (4% of the concentrating gel and 12% of the separated gel) in the conditioning stage of the hyperimmune plasma prior to the enzymatic hydrolysis, showing the composition of the hyperimmune plasma prior to the production process described in the present invention. FIG. 4 shows the formation graph of F(ab')2 fragments evaluated by SDS-PAGE and it is compared against known concentration standards, showing that under the processing conditions it is possible to achieve an efficiency of not less than 95% of F(ab')2 fragment formation. FIG. 5 shows the SDS-PAGE analysis after enzymatic digestion with pepsin. FIG. 6A shows the SDS-PAGE analysis and FIG. 6B presents the results of the molecular exclusion HPLC analysis after precipitation with ammonium sulfate. FIG. 7 shows the depth filtration stage. FIGS. 8A to 8F present the results of the molecular exclusion HPLC analysis which allows the percentage composition of the Fab, F(ab')2, dimer, soluble oligomers and low molecular weight impurities, under suitable mobile phase polarity conditions, employing a support with specific molecular exclusion characteristics and a measuring system with an ultraviolet detector at 280 nanometers. In FIGS. 8A to 8F the elution order is: soluble oligomers, dimer, F(ab')2, Fab and components of low molecular weight. Where the purity greater than 85% of F(ab')2 fragments can be seen. FIG. 9 shows the SDS-PAGE analysis for the three batches at the diafiltration stage and HPLC analysis for the ultrafiltered product in the process.

Example 4

The evaluation of the quality specifications of a lyophilized injectable pharmaceutical formula based on modified Antibodies (F(ab')2 Fragments) in accordance with the quality specifications of the FEUM (United States of Mexico Pharmacopoeia) and USP (United States Pharmacopoeia).

The production process of high specificity immunotherapeutics based on F(ab')2 fragments, as described in this invention, takes place under Good Manufacturing Practices (GMPs) guidelines, which are the guidelines allowing products to be obtained at industrial level complying with the guidelines settled in the FEUM and the USP which settles the principal properties of purity, security, concentration, identity and potency to be met by the products obtained from the process described.

The foregoing examples have been provided solely for the purpose of exemplification and are not intended to restrict the scope or the contents of the invention. The invention is described in greater detail with reference to the claims presented below.

The invention claimed is:

1. A composition comprising polyvalent venom-specific, modified antibodies obtained from mammals hyperimmunized with the venom, wherein the composition contains at least 17.7% F(ab')$_2$ fragments of the antibodies and the F(ab')$_2$ is prepared by a process comprising:
    (a) diluting hyperimmune plasma from the mammals in three volumes of sterile isotonic solution;
    (b) adjusting the pH of the diluted plasma to approximately 3.5 to 4.0 and adding activated pepsin to final concentration of approximately 0.9% to approximately 1.1%;
    (c) digesting proteins contained in the diluted hyperimmune plasma under acidic conditions at approximately 18° C. to approximately 20° C. to hydrolyze albumin, fibrinogen and coagulation factors into smaller peptides, and to separate IgG into F(ab')$_2$ fragment and fragment crystallizable (Fc) region;
    (d) adding ammonium sulfate to a final concentration of approximately 35% to precipitate components at 2° C. to 8° C.;
    (e) removing the precipitate and recovering a filtrate comprising F(ab')$_2$ fragments by depth filtration;
    (f) adjusting the pH of the filtrate to 6.8 to 7.0 and storing the filtrate at 2° C. to 8° C.;
    (g) diafiltering the filtrate by continuous tangential flow filtration using a membrane with an approximately 50 kDa cut-off while maintaining a diafiltration sheer below 1000 sec$^{-1}$;
    (h) adding cryoprotective and tonicity regulating agents and nanofiltering the diafiltered product to provide a liquid formulation; and
    (i) lyophilizing the liquid formulation.

2. The composition according to claim 1, wherein less of the F(ab')$_2$ is required to neutralize the venom in comparison to the hyperimmune plasma obtained from the mammals.

3. A method to prepare a composition comprising polyvalent venom-specific F(ab')$_2$ obtained from mammals hyperimmunized with the venom, comprising:
    (a) diluting hyperimmune plasma obtained from the mammals hyperimmunized with the venom in three volumes of sterile isotonic solution;
    (b) adjusting the pH of the diluted plasma to approximately 3.5 to 4.0 and adding activated pepsin to final concentration of approximately 0.9% to approximately 1.1%;
    (c) digesting proteins contained in the diluted hyperimmune plasma under acidic conditions at approximately 18° C. to approximately 20° C. to hydrolyze albumin, fibrinogen and coagulation factors into smaller peptides, and to separate IgG into F(ab')$_2$ fragment and fragment crystallizable (Fc) region;
    (d) adding ammonium sulfate to a final concentration of approximately 35% to precipitate components at 2° C. to 8° C.;

(e) removing the precipitate and recovering a filtrate comprising F(ab')$_2$ fragments by depth filtration;

(f) adjusting the pH of the filtrate to 6.8 to 7.0 and storing the filtrate at 2° C. to 8° C.;

(g) diafiltering the filtrate by continuous tangential flow filtration using a membrane with an approximately 50 kDa cut-off while maintaining a diafiltration sheer below 1000 sec$^{-1}$;

(h) adding cryoprotective and tonicity regulating agents and nanofiltering the diafiltered product to provide a liquid formulation; and (i) lyophilizing the liquid formulation.

4. The composition of claim 1, wherein the digesting is for approximately 180 minutes.

5. The composition of claim 1, wherein at the end of the digesting the concentration of IgG is 2% or less and the concentration of albumin is 0.5% or less.

6. The composition of claim 1, wherein the efficiency of digesting IgG into F(ab')$_2$ fragment and fragment crystallizable (Fc) region is not less than 95%.

7. The composition of claim 1, wherein diafiltering comprises filtration with 10 diafiltration volumes.

8. The composition of claim 1, wherein diafiltering is performed using borate buffer.

9. The composition of claim 1, wherein the cryoprotective and tonicity regulating agents added to provide a liquid formulation comprise mannitol, alanine, and polysorbate 80.

10. The composition of claim 9, wherein the liquid formulation comprises 9 mg/ml mannitol, 18 mg/ml alanine, and 0.1 mg/ml polysorbate 80.

11. The composition of claim 1, wherein the hyperimmunized mammals are hyperimmunized horses.

12. The method of claim 3, wherein the digesting is for approximately 180 minutes.

13. The method of claim 3, wherein at the end of the digesting the concentration of IgG is 2% or less and the concentration of albumin is 0.5% or less.

14. The method of claim 3, wherein the efficiency of digesting IgG into F(ab')$_2$ fragment and fragment crystallizable (Fc) region is not less than 95%.

15. The method of claim 3, wherein diafiltering comprises filtration with 10 diafiltration volumes.

16. The method of claim 3, wherein diafiltering is performed using borate buffer.

17. The method of claim 3, wherein the cryoprotective and tonicity regulating agents added to provide a liquid formulation comprise mannitol, alanine, and polysorbate 80.

18. The method of claim 17, wherein the liquid formulation comprises 9 mg/ml mannitol, 18 mg/ml alanine, and 0.1 mg/ml polysorbate 80.

19. The method of claim 3, wherein the hyperimmunized mammals are hyperimmunized horses.

\* \* \* \* \*